United States Patent [19]

McCue et al.

[11] Patent Number: 5,908,854
[45] Date of Patent: Jun. 1, 1999

[54] MYCOBACTERIAL COMPOSITIONS AND METHODS FOR THEIR USE

[75] Inventors: Karen Ann McCue, Tenafly; Narendra Nanavati, Maywood, both of N.J.; Timothy John Taylor, Oviedo, Fla.

[73] Assignee: Reckitt & Colman Inc., Wayne, N.J.

[21] Appl. No.: 08/928,098

[22] Filed: Sep. 12, 1997

[30] Foreign Application Priority Data

Nov. 12, 1996 [GB] United Kingdom .................... 9623476

[51] Int. Cl.⁶ ............................ A01N 43/40; A01N 33/12
[52] U.S. Cl. .......................... 514/358; 514/642; 514/643; 514/723
[58] Field of Search .................................. 252/FOR 142, 252/FOR 144; 514/643, 642, 723, 358

[56] References Cited

U.S. PATENT DOCUMENTS

| | | | |
|---|---|---|---|
| 4,455,250 | 6/1984 | Frazier | 252/106 |
| 5,185,145 | 2/1993 | Eggensperger et al. | 424/78.08 |
| 5,444,094 | 8/1995 | Malik et al. | 514/643 |

FOREIGN PATENT DOCUMENTS

| | | | |
|---|---|---|---|
| 23334 | 2/1981 | European Pat. Off. | |
| 94655 | 11/1983 | European Pat. Off. | |
| 0 621 335 A2 | 10/1994 | European Pat. Off. | C11D 1/835 |
| 0 691 397 A2 | 1/1996 | European Pat. Off. | C11D 3/00 |
| 06256106 | 9/1994 | Japan | |
| 2 095 277 | 9/1982 | United Kingdom | C11D 1/835 |

OTHER PUBLICATIONS

WPI Abstract Acc. No. 91–296375/41 and DD 0290019 A (VEB).
WPI Abstract Acc. No. 85–311753/50 and DE 3519557 A (Interkemia).
WPI Abstract Acc. No. 76–01477X/01 and SU 0466276 A (Urals).
Copy of PCT International Search Report for PCT/US97/15985 dated Dec. 19, 1997.
Copy of GB Patent Office Search Report for GB Application No. 9623476.0 dated Feb. 11, 1997.

*Primary Examiner*—Jose' G. Dees
*Assistant Examiner*—Alton Pryor
*Attorney, Agent, or Firm*—Fish & Richardson P.C.

[57] ABSTRACT

Disclosed are aqueous mycobacterial concentrate compositions at a pH in the range of 6 to 12 which comprises per 100% weight of a concentrate composition:

a) from about 0.1% wt. to about 25% wt. of a germicidal cationic quaternary ammonium compound;

b) from about 0.25% wt. to about 25% wt. of a solvent selected from: phenoxyalcohol, glycol ethers, or mixtures thereof; and, c) water.

The concentrate compositions may be used in a ready to use form, or may be further diluted with water to form a disinfecting composition therefrom. The compositions may also include an effective amount of a pH adjusting agent, such as sodium hydroxide or triethanolamine. The compositions featuring reduced amounts of active constituents than those known to the art, and are particularly effective against *Mycobacteriuin terrae*.

13 Claims, No Drawings

MYCOBACTERIAL COMPOSITIONS AND METHODS FOR THEIR USE

FIELD OF THE INVENTION

The present invention relates to disinfectant compositions and methods for their use. More particularly, the present invention relates to disinfectant compositions which are effective against *Mycobacterium terrae.*

BACKGROUND ART

Disinfectant compositions containing quaternary ammonium compounds as cationic active antimicrobial agents are known in the art. Many marketed quaternary disinfectant compositions exhibit broad spectrum bactericidal, fungicidal and virucidal activity but they are not mycobactericidal. There are a few known registered disinfectants that contain such quaternary compound and claim mycobactericidal activity but these are generally used in combination with other known active agents (e.g., tributyl tin oxide, isopropanol). Such products contain other active compounds and/or high concentrations of quaternary ammonium compounds and require detailed directions for use in order to avoid possible toxic or other adverse reactions.

Although many virucidal, bactericidal, sporicidal, and fungicidal compositions are known, none is currently available that provides highly efficacious elimination of mycobacteria while providing low toxicity, no odor, non-flammability, low skin irritation and no staining upon contact with a surface. Mycobacteria are resistant to treatment by most bactericidal compounds. Their trilaminar cell walls, composed of 60% lipid, peptidoglycan, arabinoglycan, trehalose 6,6 dimycolate, sulfates and mycosides, accounts for the unusual properties of the organism: (a) relative impermeability to stains, (b) acid fastness, and (c) unusual resistance to killing by acid or alkali.

In U.S. Pat. No. 5,185,145, Eggensperger et al. disclose a mycobactericidal disinfectant concentrate comprising 0.1–50% by weight of a cationic active compound, 10–60% by weight of a phenoxyalcohol mixture, 3–25% by weight of a non-ionic surfactant and 0.1–10% by weight of an organic-nitrogen containing base to effect a pH range of 7.8–11. One disadvantage displayed by this preparation is that relatively high concentrations of the active ingredients in an alkaline pH range are needed to achieve disinfection in a practical short contact time.

For the purpose of disinfecting surfaaces, lower concentrations of the active agents and a neutral pH range are desirable from the standpoint of cost-effectiveness, safety and aesthetics.

It is a principal object of this invention to provide a mycobactericidal disinfectant composition which overcomes one or more of the aforementioned technical shortcomings in the art.

It is a further object of the invention to provide an aqueous mycobactericidal disinfectant composition containing a cationic quaternary ammonium compound and a solvent system that would provide mycobactericidal activity at lower active concentrations and at lower pH ranges than known art mycobactericidal disinfectant compositions.

It is a still further object of the invention to provide a mycobactericidal disinfectant composition in the form of a cost effective, safe and aesthetically practical, ready-to-use or dilutable disinfectant product.

SUMMARY OF THE INVENTION

These and other objects of the invention are satisfied by an aqueous mycobactericidal concentrate composition at a pH in the range of from about 6.0 to about 12.0 which comprises per 100% weight of a concentrate composition:

a) from about 0. 1% wt. to about 25% wt. of a germicidal cationic quaternary ammonium compound;

b) from about 0.25% wt. to about 25% wt. of a solvent selected from phenoxyalcohol, glycol ethers, or mixtures thereof; and, c) water.

Detailed Disclosure

Useful quaternary ammonium compounds and salts thereof include quaternary ammonium germicides which may be characterized by the general structural formula:

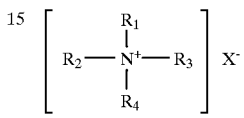

where at least one of R1, R2, R3 and R4 is a hydrophobic, aliphatic, aryl aliphatic or aliphatic aryl radical of from 6 to 26 carbon atoms, and the entire cation portion of the molecule has a molecular weight of at least 165. The hydrophobic radicals may be long-chain alkyl, long-chain alkoxy aryl, long-chain alkyl aryl, halogen-substitued long-chain alkyl aryl, long-chain alkyl phenoxy alkyl, etc. The remaining radicals on the nitrogen atoms other than the hydrophobic radicals are substituents of a hydrocarbon structure usually containing a total of no more than 12 carbon atoms. The radicals R1, R2, R3 and R4 may be straight chained or may be branched, but are preferably straight chained, and may include one or more amide or ester linkages. The radical X may be any salt-forming anionic radical.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide or ester linkages such as octyl phenoxy ethoxy ethyl dimethyl benzyl ammonium chloride, N-(laurylcocoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

Preferred quaternary ammonium compounds which act as germicides and which are be found useful in the practice of the present invention include those which have the structural formula:

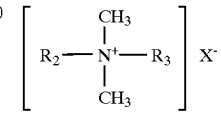

wherein R2 and R3 are the same or different C8–C12alkyl radicals or wherein R2 is C12–16alkyl, C8–18alkylethoxy, C8–18alkylphenolethoxy and R3 is benzyl, and X is a halide, such chloride, bromide or iodide, or is a methosulfate. The alkyl groups recited in R2 and R3 may be straight chained or branched, but are preferably substantially linear.

Particularly useful quaternary germicide compositions include compositions which have a single quaternary compound, as well as mixtures of two or more different quaternaries. Particularly useful quaternary germicides include BARDAC® 205M, and BARDAC® 208M or BTC® 885 which are described to be a blend of alkyl dimethyl benzyl armnonium chlorides; BARDAC® 2050 and BARDAC(® 2080 or BTC® 818 which are described to be based on dialkyl(C8–C10)dimethyl ammonium chloride; BARDAC® 2250 and BARDAC® 2280 or BTC® 1010 which are described to a composition which includes didecyl dimethyl ammonium chloride; BARDAC® LF and BARDAC® LF 80 which are described to be based on dioctyl dimethyl ammonium chloride; BARQUAT® MB-50, HYAMINE® 3500, BARQUAT® MB-80, BTC® 835 or BTC 8358, each described to be based on alkyl dimethyl benzyl ammonium chloride; BARQUAT® MX-50, BARQUAT® MX-80, BTC® 824 or BTC® 8248 each described to be a composition based on alkyl dimethyl benzyl ammonium chloride; BARQUAT® OJ-50, BARQUAT® OJ-80, BTC® 2565 or BTC® 2658, each described to be a composition based on alkyl dimethyl benzyl ammonium chloride; BARQUAT® 4250, BARQUAT® 4280, BARQUAT® 4250Z, BARQUAT® 4280Z, BTC® 2125 or BTC® 2125M, each described to be a composition based on alkyl dimethyl benzyl ammonium chloride and/or alkyl dimethyl ethyl benzyl ammonium chloride; BARQUAT® MS-100 or BTC® 324-P-100 each described to be based on myristyl dimethyl benzyl ammonium chloride; HYAMINE® 2389, described to be based on methyl dodecyl benzyl ammonium chloride and/or methyl dodecyl xylene-bis-trimethyl ammonium chloride; HYAMINE® 1622, described to be an aqueous solution of benzethonium chloride; HYAMINE® 3500-NF or BTC® 50, each described to be based on alkyl dimethyl benzyl ammonium chloride; as well as BARQUAT® 1552 or BTC® 776, described to be based on alkyl dimethyl benzyl ammonium chloride and/or dialkyl methyl benzyl ammonium chloride. (All of these recited materials are commercially available from Lonza, Inc., Fairlawn, N.J. or from Stepan Co., Northfield Ill.) Especially preferred gernidical cationic quaternary ammonium compounds include those described in one or more of the example formulations, below.

As noted, the germicidal cationic quaternary ammonium compound is present in an amount of from about 0.1% wt. to about 25% wt, and desirably is present in substantially reduced amounts of from 0.1% wt. to 5% wt., more desirably from 0.1% wt. to 2.5% wt., and particularly from 0.1% wt to 0.3% wt.

The solvents according to the invention are selected from phenoxyalcohols, glycol ethers, or mixtures thereof.

Useful glycol ethers are those having the general structure Ra—O—Rb—OH, wherein Ra is an alkoxy of 1 to 20 carbon atoms, or aryloxy of at least 6 carbon atoms, and Rb is an ether condensate of propylene glycol and/or ethylene glycol having from one to ten glycol monomer units. Examples of preferred solvents include diethylene glycol n-butyl ether, propylene glycol n-butyl ether, propylene glycol n-propyl ether, dipropylene glycol n-butyl ether, dipropylene glycol methyl ether, as well as mixtures thereof. Of these, the more preferred are diethylene glycol n-butyl ether and propylene glycol n-butyl ether, especially mixtures thereof. Most preferred is propylene glycol phenyl ether used singly, or in a mixture with at least one further glycol ether, especially diethylene glycol n-butyl ether and propylene glycol n-butyl ether. These glycol ethers are commerically available in the Dowanol® glycol ether series available from The Dow Chemical Company (Midland, Mich.) or in the Carbitol® series from Union Carbide.Co. (Danbury, Conn.).

The mycobacterial concentrate compositions according to the invention are in the pH range of about 6.0 to about 12.0 and such may require the use of a pH adjusting agent. Known inorganic compounds such as alkali metal hydroxides, and/or organic nitrogen-containing compounds may be used to provide this pH adjustment. When such a pH adjusting agent is necessary, desirably it is an alkanolamine compound, particularly an ethanolamine such as mono-, di- or tri-ethanolamine. The pH adjusting compound is needed only in a sufficient amount to adjust the composition to the pH range noted above. One or more ingredients may optionally be included in order to provide aesthetic or other beneficial properties thereto; generally these are included in only minor amounts, i.e., in total comprising not more than about 2.5% wt. of the total mycobacterial concentrate compositions. Such optional ingredients include, by way of non-limiting example, fragrances, surfactants, additional microbial agents, emulsifiers, chelating agents, and rheology-adjusting agents, pH buffer agents. The only requirement is that, for any particular composition, such optional ingredients be compatible with the other ingredients therein. Typical chelating agents such as ethylenediaminetetraacetate (EDTA) may be used. Fragrances derived from naturally occuring sources and/or those which are synthetically produced may be used. A fragrance solubilizer may form part of the fragrance constituent. Anionic, cationic, amphoteric, and non-ionic surfactants, such as nonionic ethoxylated alkylphenols may be used to enhance the membrane solubilizing capabilities of the composition. Such membrane solubilizing characteristics may be particulary advantageous in improving the transfer of the germicidal quaternary ammonium compound across the cell wall of a bacteria or virus.

These compositions according to the invention are preferably employed "as is", namely as a ready-to-use composition without further dilution. (The inventive compositions also include concentrates which are dilutable in a larger volume of water.) The mycobacterial concentrate compositions may be dissolved in water in a weight or volume ratio of concentrate composition: water from 1:0–1:250. Such aqueous disinfecting solutions which comprise the mycobacterial concentrate compositions described herein are to be understood to also form part of the instant invention.

The inventive compositions may be used in a wide variety of disinfecting applications and in a wide variety of environments which may benefit from a disinfecting effect, especially in the disinfection of surfaces wherein the presence of mycobacteria is suspected. These applications and environments include usage in the medical sector for the disinfection of instruments and apparatuses, as well as for disinfection or decontamination of operating theatres and fixtures therein. The use of the compositions for the disinfection or decontamination of hospital environments including lavatories and lavatory fixtures hospitals, clinics, examining rooms, and other environments associated with the provision of healthcare services and wherein the presence of mycobacteria are suspected is also expressly contemplated. Such environments are to be understood to include not only the surfaces of walls, ceilings and floors, but to specifically include other surfaces such as the surfaces of various health care apparatus which may be found in such environments wherein healthcare surfaces are provided. The use of the inventive compositions provides an effective and simple to use method for the disinfection of such environments which concomitantly reduces the risk of mycobacterial infection.

The inventive compositions are particularly to be understood to include hard surfaces. By way of example, hard surfaces suitable for coating with the polymer include surfaces composed of refractory materials such as: glazed and unglazed tile, brick, porcelain, ceramics as well as stone including marble, granite, and other stones surfaces; glass; metals; plastics e.g. polyester, vinyl; fiberglass, Formica®, Corian® and other hard surfaces known to the industry. Hard surfaces which are to be particularly denoted are lavatory fixtures such as shower stalls, bathtubs and bathing appliances (racks, curtains, shower doors, shower bars) toilets, bidets, wall and flooring surfaces especially those which include refractory materials and the like. Further hard surfaces which are to be denoted are those associated with kitchen environments and other environments associated with food preparation, including cabinets and countertop surfaces as well as walls and floor surfaces especially those which include refractory materials, plastics, Fiberglass®, Formica®, Corian® and stone.

The concentrate compositions as well as aqueous dilutions of the concentrate compositions according to the invention can be desirably provided as a ready to use product in a manually operated spray dispensing container. Such a typical container is generally made of synthetic polymer plastic material such as polyethylene, polypropylene, polyvinyl chloride or the like and includes spray nozzle, a dip tube and associated pump dispensing parts and is thus ideally suited for use in a consumer "spray and wipe" application. In such an application, the consumer generally applies an effective amount of the composition using the pump and a short time thereafter, wipes off the treated area with a rag, towel, or sponge, or other material. In this manner, disinfection of the treated surface may be achieved.

In a yet a further embodiment, the composition according to the invention may be formulated so that it may be useful in conjunction with a "aerosol" type product wherein it is discharged from a pressurized aerosol container. Known art propellants such as liquid propellants based on chlorofluorocarbons or propellants of the non-liquid form, i.e., pressurized gases, including carbon dioxide, air, nitrogen, as well as others, may be used, even though it is realized that the former chlorofluorocarbons are not generally further used due to environmental considerations. In such an application, a composition according to the invention is dispensed by activating the release nozzle of said aerosol type container onto a surface in need of disinfection, and generally in accordance with a manner as above-described is removed with the use of a rag, towel, or sponge, or other material.

It is to be understood that the compositions according to the invention may be applied to a surface which is in need of disinfection, particularly where the presence of mycobacteria is suspected.

One skilled in the art will recognize that modifications may be made in the present invention without deviating from the spirit or scope of the invention. The invention is illustrated further by the following examples which are not to be construed as limiting the invention or scope of the specific procedures described herein

EXAMPLES

Various examples within the scope of the present invention, including those which embody preferred examples of the invention, as well as further formulations which are provided for purposes of comparison are described on Table 1, below. The weight percentages reported in Table 1 are the percent weight ("% wt.") of the indicated constituent incorporated into a respective formulation which comprised 100% wt.

TABLE 1

| constituent: | C1 | C2 | Ex. 1 | Ex. 2 | Ex. 3 | Ex. 4 |
|---|---|---|---|---|---|---|
| Didecyl-dimethyl quaternary ammonium salt | 0.2 | — | 0.2 | 0.2 | 0.2 | 0.1 |
| propylene glycol phenyl ether | — | 1.5 | 0.5 | 1.5 | 0.25 | 0.25 |
| Triethanol-amine | 0.026 | 0.026 | 0.026 | — | 0.026 | 0.026 |
| NaOH | — | — | — | — | 0.17 | 0.15 |
| DI water | to 100 | to 100 | to 100 | to 100 | to 100 | to 100 |
| pH | 9.4 | 9.6 | 9.3 | 6.0 | 12 | 12 |

The commercial sources of the individual constituents denoted on Table 1 are described in more detail on Table 2, below.

TABLE 2

| | |
|---|---|
| Didecyldimethyl quaternary ammonium sodium salt | BARDAC ® 2280 |
| propylene glycol phenyl ether | Dowanol ® PPH |
| Triethanolamine | triethanolamine |
| NaOH | sodium hydroxide |
| DI water | deionized water |

In the compositions of Table 1, the triethanolamine and NaOH are provided as pH adjusting agents. Formulations according to the invention include Ex.1, Ex.2, Ex.3 and Ex.4, while comparative example formulations are C1 and C2.

Each of the formulations of Table 1 was evaluated for mycobactericidal activity against the test organism *Mycobacterium terrae*. A substrate test similar to "AOAC Confirmative In Vitro Test for Determining Tuberculocidal Activity", AOAC Official Methods of Analysis, 15th ed. 1990, pg. 142–143 was used. This testing protocol is as follows.

Microbial substrate tests were conducted with the test organism *Mycobacterium terrae* (ATCC #15755). Stock cultures of *Mycobacterium terrae* are grown and maintained on Difco's Lowenstein Medium, Jensen agar slants and stored at 2–5° C. The culture suspension was prepared by washing the stock culture slant with phosphate buffer saline solution. With a sterile cotton swab, a fresh slant of Lowenstein Medium, Jensen Agar was used to inoculate the slant. The slant was then incubated at 37° C. for 10 days. After 10 days, each slant was washed with 10 ml. saline. Subsequently the saline culture was transferred to a tissue grinder and macerated to a smooth culture. This macerated *Mycobacterium terrae* culture suspension was used to soak porcelain cylinders. At least a 10 ml. culture was needed to soak 10 cylinders in the test. A phenol resistance test was also conducted on the inoculum following the procedure in accordance with AOAC protocols. A thus prepared inoculum exhibiting a phenol resistance of 1:50–1:60 was judged to be satisfactory and used in subsequent steps.

Porcelain penicylinders were the substrates in accordance with standard AOAC procedures which were used in the subsequent procedures. First, the penicylinders were sterilized and prepared according to the standardized AOAC procedure. Sterile porcelain penicylinders were subsequently soaked in the *Mycobacterium terrae* standard culture suspension, as prepared above, for 15 minutes at room temperature (approx. 20° C.). Afterwards, the soaked penicylinders were aseptically removed to a sterile petri dish matted with filter paper and allowed to dry at 37° C. ±1° C. for 40 minutes. While the inoculated cylinders were drying, medicant tubes containing 10 mls. each of the test formulations (see Table 1) were prepared and held at 20° C. (i.e. for a 30 cylinder test, 30 tubes each containing 10 ml. of test formulation was prepared).

After the inoculated cylinders were dried, each cylinder was added to a medicant tube containing 10 ml. of the test formulation (i.e., one cylinder/10 ml. test formulation) and permitted to remain in contact with the test formulation for 10 minutes. After 10 minutes, each cylinder was aseptically subcultured into 10 ml. of modified BBL Trypticase Soy Broth neutralizer medium (TSB containing 3% Tween 80, 3% saponin, 0. 1% Histidine and 0.1% cystein) for 15 minutes. After this time, each cylinder was aseptically subcultured to 10 ml. BBL's 7H9 broth growth medium containing 0.1 ml. Difco's Middlebrook ADC enrichment to support growth of surviving organisms. For each of the evaluated formulations, a total of at least 30 cylinders were evaluated. The tubes containing the cylinders were incubated at 37° C. for 42 days. After this time, tubes were visually observed for growth (white clumps, particulate) or no growth. Mycobactericidal activity was considered to have been achieved if no growth of *Mycobacterium terrae* was observed with 30 cylinders.

As an experimental "control", two untreated inoculated cylinders were also subcultured in 7H9 broth with enrichment, then vortexed and plate counts were conducted on a sample of the inoculated broth in order to enumerate the number of survivors from the cylinder after drying. Difco's 7H 11 Agar with Difco's Middlebrook OADC enrichment was used to enumerate survivors.

The results of this evaluation are reported on Table 3, as the number of penicylinders having growth/number of penicylinders in the test sample.

TABLE 3

| Formulation: | C1 | C2 | Ex. 1 | Ex. 2 | Ex. 3 | Ex. 4 |
|---|---|---|---|---|---|---|
| Penicylinders with growth/ total cylinders tested | 11/30 | 47/60 | 0/60 | 0/30 | 0/30 | 0/30 |

As may be seen from the test results, the comparative formulations C1 and C2, each containing only one critical component in an alkaline pH range, did not show mycobactericidal activity. The formulations according to the invention, especially the formulation according to Examples 1 and 2 containing both critical components of the specific quaternary and the specific solvent, demonstrated excellent mycobactericidal activity. Each of these critical components is in a low concentration range and at a neutral or alkaline pH.

We claim:

1. A hard surface disinfecting composition which comprises an aqueous mycobacterial concentrate which consists essentially of:

a) from about 0.10% wt. to about 25% wt. of a germicidal cationic quaternary ammonium compound;

b) from about 0.25% wt. to about 25% wt. of a solvent selected from phenoxyalcohol, or mixtures of phenoxyalcohols and glycol ethers; and, c) to 100% wt. water wherein the hard surface disinfecting compositions at a pH in the range of from about 6 to about 12.

2. A hard surface disinfecting composition according to claim 1 which further comprises one or more optional constituents selected from: fragrances, surfactants, additional microbial agents, emulsifiers, chelating agents, rheology-adjusting agents, pH adjusting agents, and pH buffering agents.

3. A disinfecting composition comprising the aqueous mycobacteral concentrate composition according to claim 1 dissolved in water in a weight or volume ratio of mycobacterial concentrate composition.water of from 1:0 to 1:250.

4. A hard surface disinfecting composition according to claim 1 which comprises a pH adjusting agent or a pH buffering agent.

5. A method of disinfecting a hard surface where myrcobacteria are suspected which comprises the process step of: contacting the hard surface with an effective amount of the aqueous myrcobacterial concentrate composition according to claim 1.

6. A hard surface disinfecting composition according to claim 2 which includes triethanolamine.

7. A hard surface disinfecting composition according to claim 1 which further comprises one or more optional constituents selected from: fragrances, surfactants, additional microbial agents, emulsifiers, chelating agents, rheology-adjusting agents, pH adjusting agents, and pH buffering agents.

8. A hard surface disinfecting composition which comprises an aqueous mycobacterial concentrate which consists essentially of:

a) from about 0.10% wt. to about 25% wt. of a germicidal cationic quaternary ammonium compound;

b) from about 0.25% wt. to 1.5% wt. of one or more glycol ethers having the general structure Ra—O—Rb—OH, wherein Ra is an alkoxy of 1 to 20 carbon atoms, or aryloxy of at least 6 carbon atoms, and Rb is an ether condensate of propylene glycol and/or ethylene glycol having from one to ten glycol monomer units; and, c) to 100% wt. water wherein the hard surface disinfecting compositions at a pH in the range of from about 6 to about 12.

9. A hard surface disinfecting composition according to claim 8 which further comprises one or more optional constituents selected from: fragrances, surfactants, additional microbial agents, emulsifiers, chelating agents, rheology-adjusting agents, pH adjusting agents, and pH buffering agents.

10. A hard surface disinfecting composition according to claim 9 which comprises a pH adjusting agent or a pH buffering agent.

11. A hard surface disinfecting composition according to claim 10 which includes triethanolamine.

12. A disinfecting composition composing the aqueous mycobacterial concentrate composition according to claim 8 dissolved in water in a weight or volume ratio of mycobacterial concentrate composition:water of from 1:0 to 1:250.

13. A method of disinfecting a hard surface where mycobacteria are suspected which comprises the process step of contacting the hard surface with an effective amount of the aqueous mycobacterial concentrate composition according to claim 8.

* * * * *

UNITED STATES PATENT AND TRADEMARK OFFICE
CERTIFICATE OF CORRECTION

PATENT NO. : 5,908,854
DATED : 01 June 1999
INVENTOR(S) : Karen Ann McCUE; Narendra NANAVATI
Timothy John TAYLOR It is certified that error appears in the above-indentified patent and that said Letters Patent is hereby corrected as shown below:

At column 8, line 9, delete "mycobacteral" and insert -- mycobacterial--.

At column 8, line 11, delete the "." after "composition" and insert --:--.

At column 8, lines 15-16, delete "myrcobacteria" and insert --mycobacteria--.

At column 8, line 18, delete "myrcobacterial" and insert --mycobacterial--.

At column 8, line 62, after the words "step of" insert --:--.

Signed and Sealed this

Nineteenth Day of October, 1999

Attest:

Q. TODD DICKINSON

Attesting Officer

Acting Commissioner of Patents and Trademarks